(12) United States Patent
Martens et al.

(10) Patent No.: US 7,230,151 B2
(45) Date of Patent: *Jun. 12, 2007

(54) TWO CATALYST PROCESS FOR MAKING OLEFIN

(75) Inventors: Luc R. M. Martens, Meise (BE); Keith H. Kuechler, Friendswood, TX (US); James R. Lattner, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/891,975

(22) Filed: Jul. 15, 2004

(65) Prior Publication Data

US 2004/0254413 A1   Dec. 16, 2004

Related U.S. Application Data

(63) Continuation of application No. 09/943,610, filed on Aug. 30, 2001, now Pat. No. 6,797,851.

(51) Int. Cl.
C07C 1/20 (2006.01)

(52) U.S. Cl. ............ 585/324; 585/327; 585/639; 585/640

(58) Field of Classification Search ............ 585/324, 585/327, 639, 638, 640
See application file for complete search history.

(56) References Cited

U.S. PATENT DOCUMENTS

| | | | |
|---|---|---|---|
| 3,258,455 A | 6/1966 | Natta et al. | 260/93 |
| 3,305,538 A | 2/1967 | Natta et al. | 260/93 |
| 3,364,190 A | 1/1968 | Emrick | 260/93 |
| 3,645,992 A | 2/1972 | Elston | 260/80 |
| 3,702,886 A | 11/1972 | Argauer et al. | 423/328 |
| 4,016,245 A | 4/1977 | Plank et al. | 423/328 |
| 4,058,476 A | 11/1977 | Boller et al. | 252/299 |
| 4,058,576 A | 11/1977 | Chang et al. | 260/673 |
| 4,076,698 A | 2/1978 | Anderson et al. | 526/348 |
| 4,243,691 A | 1/1981 | Mohlenkamp, Jr et al. | 426/649 |

(Continued)

FOREIGN PATENT DOCUMENTS

DE    32 09 223    9/1983

(Continued)

OTHER PUBLICATIONS

Sun, et al., "The Catalytic Conversion of Methyl Chloride to Ethylene and Propylene over Phosphorous-Modified Mg-ZSM-5 Zeolites", *J. Catal.*, vol. 143, pp. 32-44 (1993).

(Continued)

*Primary Examiner*—Thuan Dinh Dang
(74) *Attorney, Agent, or Firm*—David M. Weisberg

(57) ABSTRACT

This invention is to a process of making olefin, particularly ethylene and propylene, from an oxygenate feed. The invention uses two or more zeolite catalysts. Examples of zeolite catalysts include a first catalyst containing of ZSM-5, and a second catalyst containing a 10-ring molecular sieve, including but not limited to, ZSM-22, ZSM-23, ZSM35, ZSM-48, and mixtures thereof. The ZSM-5 can be unmodified, phosphorous modified, steam modified having a micropore volume reduced to not less than 50% of that of the unsteamed ZSM-5, or various mixtures thereof.

8 Claims, 5 Drawing Sheets

U.S. PATENT DOCUMENTS

| | | | |
|---|---|---|---|
| 4,302,565 A | 11/1981 | Goeke et al. | 526/88 |
| 4,499,327 A | 2/1985 | Kaiser | 585/640 |
| 4,542,252 A | 9/1985 | Graziani et al. | 585/640 |
| 4,582,815 A | 4/1986 | Bowes | 502/64 |
| 4,659,685 A | 4/1987 | Boleman, III et al. | 502/113 |
| 4,681,864 A | 7/1987 | Edwards et al. | 502/63 |
| 4,849,575 A | 7/1989 | Lewis | 585/640 |
| 5,026,935 A | 6/1991 | Leyshon et al. | 585/315 |
| 5,026,936 A | 6/1991 | Leyshon et al. | 585/315 |
| 5,043,522 A | 8/1991 | Leyshon et al. | 585/651 |
| 5,053,374 A | 10/1991 | Absil et al. | 502/64 |
| 5,182,242 A | 1/1993 | Marler | 502/66 |
| 5,573,990 A | 11/1996 | Wang et al. | 502/77 |
| 5,892,079 A | 4/1999 | Wilson, Jr. | 556/11 |
| 5,914,433 A | 6/1999 | Marker | 585/313 |
| 5,990,369 A | 11/1999 | Barger et al. | 585/640 |
| 6,048,816 A * | 4/2000 | Brown et al. | 502/77 |
| 6,049,017 A | 4/2000 | Vora et al. | 585/324 |
| 2001/0002426 A1 | 5/2001 | Mohr et al. | 585/407 |

FOREIGN PATENT DOCUMENTS

| | | |
|---|---|---|
| DE | 3524890 | 1/1986 |
| EP | 109060 | 3/1987 |
| EP | 109059 | 7/1987 |
| GB | 2171718 | 9/1986 |
| WO | WO 97/45198 | 4/1997 |
| WO | WO 00/66263 | 9/2000 |

OTHER PUBLICATIONS

Ohlmann, et al., "Catalysis and Absorption by Zeolites", *Studies of Surface Science Catalysis*, vol. 65, pp. 1-20 (1991).

Zenz et al., *Riser Reactor, Fluidization and Fluid-Particle Systems*, Reinhold Publishing Corp. NY, pp. 48-59 (1960).

* cited by examiner

TWO CATALYST PROCESS FOR MAKING OLEFIN

CROSS REFERENCE TO RELATED APPLICATIONS

This application is a continuation application of U.S. patent application Ser. No. 09/943,610, filed Aug. 30, 2001 now U.S. Pat. No. 6,797,851, which has been allowed.

FIELD OF THE INVENTION

The present invention is in the field of converting an oxygenate to an olefin composition.

BACKGROUND OF THE INVENTION

Ethylene is an important petrochemical. In 1998 about 80 million tons of ethylene was produced, and demand is expected to reach 100 million tons by 2003. The primary use for ethylene is as a monomer for the production of low and high density polyethylene. Approximately 60% of world ethylene consumption goes into making polyethylene for such products as plastic films, containers, and coatings. Other uses for ethylene include the production of vinyl chloride, ethylene oxide, ethylbenzene and alcohols. Presently, about 90% of the ethylene is produced by the steam cracking of light paraffin, naptha, and gas oil.

Propylene is another important raw material. In 1998 about 46 million tons of propylene was produced, and demand is expected to reach 60 million tons by 2003. About 55% of the world consumption is directed to the production of polypropylene. Other important end products using propylene include acrylonitrile for acrylic and nylon fibers, and propylene oxide for polyurethane foams. About two-thirds of the propylene is produced from steam cracking, and the remaining third as a by-product of FCC gasoline refining.

A potential alternative to producing ethylene and propylene from petroleum feedstock is to use an oxygenate feedstock. Particularly promising oxygenate feedstocks are alcohols, such as methanol and ethanol, dimethyl ether, methyl ethyl ether, diethyl ether, dimethyl carbonate, and methyl formate. Many of these oxygenates can be produced from a variety of sources including synthesis gas derived from natural gas; petroleum liquids; and carbonaceous materials, including coal. Because of the wide variety of these relatively inexpensive sources, alcohol and other oxygenates have promise as an economical, non-petroleum source for ethylene and propylene production.

One way of producing ethylene and propylene is by the catalytic conversion of methanol using a silicoaluminophosphate (SAPO) molecular sieve catalyst. For example, U.S. Pat. No. 4,499,327 discloses making olefins from methanol using SAPO molecular sieve catalysts. The advantage of using SAPO catalysts is that such catalysts have relatively high ethylene and propylene selectivities.

U.S. Pat. No. 6,049,017 teaches the use of a SAPO-34 catalyst to first convert methanol to an olefin hydrocarbon product. The ethylene and propylene are then separated from the olefin hydrocarbon product. Di-olefin, such as butadiene, is selectively hydrogenated, and any isobutene is catalytically converted to methyl-t-butylether before the remainder of the olefin-hydrocarbon stream is directed to a second reaction zone. The second reaction zone is a cracking unit that converts a portion of the olefin-hydrocarbon stream to additional ethylene and propylene using SAPO-34 catalyst.

U.S. Pat. No. 5,914,433 teaches a one catalyst system to increase ethylene yields by cracking the butylene produced during the oxygenate conversion reaction. The cracking of the butylene may take place in a second conversion zone within the oxygenate conversion reactor, or in an external reaction unit. If an external reaction unit is used, the catalyst from the regenerator is used to convert the butylene to additional ethylene. In either case, the same catalyst is used for oxygenate conversion and for the butylene cracking.

GB 2171718 teaches that a zeolite catalyst, particularly a dealuminated, mordenite zeolite can be used to convert an oxygenate to a product containing olefin. The olefin product from this reaction is then separated into ethylene and propylene and a $C_4^+$ olefin portion that contains butenes. The $C_4^+$ olefin is then recycled back to the oxygenate conversion reactor to produce additional ethylene and propylene. DE 3524890 teaches that ZSM-5 can be used to convert butenes to ethylene and propylene.

Methods are known for increasing the production of ethylene and propylene from a conventional catalyst or steam cracker by a disproportionation or metathesis of the produced butenes. In U.S. Pat. No. 5,026,935, propylene and butenes are directed to a reaction zone containing a metathesis catalyst, e.g., $MoO_x$ or $WO_x$, to produce more ethylene. Similarly, in U.S. Pat. No. 5,026,936 ethylene and butenes are directed to a reaction zone using a metathesis catalyst to produce more propylene. U.S. Pat. No. 5,990,369 also describes the potential benefit of providing an olefin metathesis reaction unit to maximize ethylene or propylene yield from an oxygenate feedback.

U.S. Pat. No. 6,048,816 teaches a phosphorous modified ZSM-5 catalyst for the conversion of methanol to light olefin. The catalyst converts methanol to a light olefin stream containing over 30% by weight of ethylene and propylene.

European Patents 0 109 059 B and 0 109 060 B teach the use of ZSM-5, a modified ZSM-5, or ZSM-11 to convert butenes to propylene and smaller amounts of ethylene at temperatures between 400° C. to 600° C.

U.S. Pat. No. 5,043,522 to Leyshon teaches that a feed containing 40 to 95 wt. % paraffin having 4 or more carbon atoms and 5 to 60 wt. % olefins having 4 or more carbon atoms will produce more ethylene and propylene than if the two streams were directed to separate catalytic cracking units. The preferred catalyst for such a zeolitic cracking process are of the ZSM-type, particularly ZSM-5, and borosilicates.

U.S. Pat. No. 4,681,864 discloses that SAPO molecular sieve, particularly SAPO-37 catalyst, has an alternative use as a cracking catalyst. However, Edwards indicates that activated SAPO molecular sieves have poor storage stability.

The references suggest that SAPO molecular sieves are preferred over zeolite molecular sieves for converting oxygenates, particularly methanol, to obtain significant quantities of ethylene and propylene. However, SAPO molecular sieves are reported to have poor storage stability. It would, therefore, be advantageous to obtain significant quantities of ethylene and propylene using catalysts which have good storage stability.

SUMMARY OF THE INVENTION

The invention uses at least two different zeolite catalysts, for example, two different ZSM-type catalysts, to produce olefin having a significant quantity of ethylene and propylene. The catalysts can be mixed together in one reactor, arranged in separate beds, or used in separate reactors in series.

It is desirable that one of the zeolite catalysts contains a ZSM-5 molecular sieve. The ZSM-5 molecular sieve is selected from the group consisting of an unmodified ZSM-5, a phosphorous modified ZSM-5, a steam modified ZSM-5 having a micropore volume reduced to not less than 50% of that of the unsteamed ZSM-5, and mixtures thereof. It is also desirable to have a second zeolite catalyst which contains a zeolite molecular sieve selected from the group consisting of 10-ring zeolites such as ZSM-22, ZSM-23, ZSM-35, ZSM-48, and a mixture thereof. According to another embodiment, it is desirable to have a second zeolite catalyst which contains a zeolite molecular sieve selected from the group consisting of ZSM-22, ZSM-35, and mixtures thereof.

The invention also provides a method of making an olefin composition which comprises contacting an oxygenate with a first zeolite catalyst to form an olefin product; separating a butylene containing stream from the olefin product; and contacting the butylene containing stream with a second zeolite catalyst to form a second olefin product. The separation and subsequent contact of the butene containing stream can result in additional increase in ethylene and propylene content.

BRIEF DESCRIPTION OF THE DRAWINGS

Alternative embodiments of the invention are shown in the attached drawings, wherein.

DETAILED DESCRIPTION OF THE INVENTION

Figure 1:
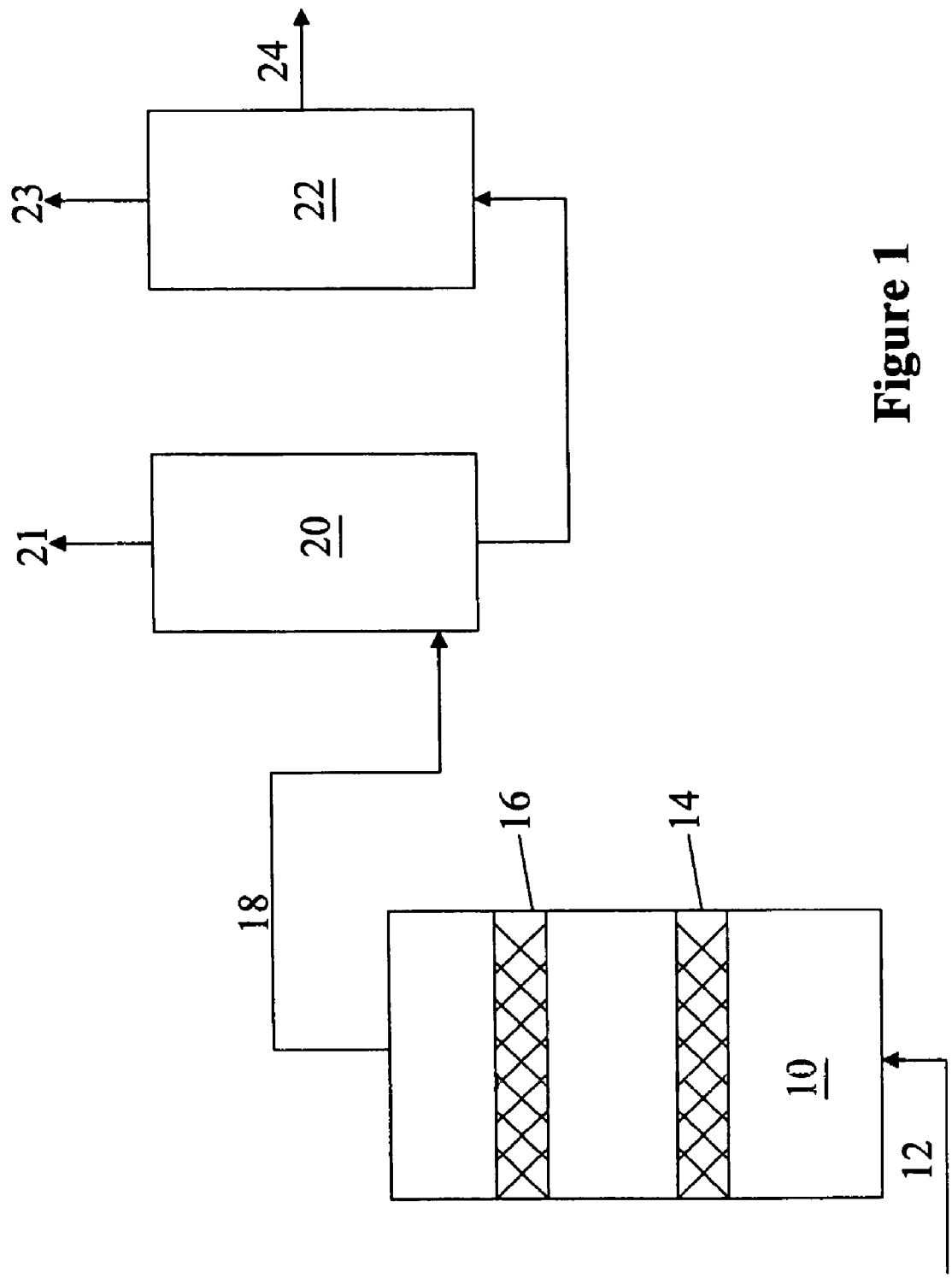
FIG. 1 is a schematic of a stacked bed reactor for carrying out the process of the invention.

This invention is directed to a method of producing olefin, particularly ethylene and propylene, from an oxygenate feed, particularly a methanol feed. The method incorporates the use of at least two zeolite catalysts.

Activated zeolite catalysts have good storage stability, and the use of two different zeolites can provide excellent selectivity to ethylene and propylene formation. ZSM type zeolite catalysts are examples of such zeolite catalysts which can be used in this invention.

The zeolite catalysts can be mixed and used in a single reactor; they can be separated into different beds; or they can be separated into different reactors. Particularly good results are obtained when a first zeolite catalyst is used to contact the oxygenate; a butene containing fraction is separated from the resulting product; and the separated butene containing fraction is contacted with a second zeolite.

In one embodiment, the conversion to ethylene and propylene is enhanced using a two stage process. In the first stage, oxygenate contacts a zeolite catalyst, preferably containing ZSM-5, more preferably a phosphorous modified ZSM-5 (P-ZSM-5). The resulting oxygenate conversion product contains ethylene, propylene, and butenes (or butylenes) and higher olefin ($C_4^+$ olefin) composition. The $C_4^+$ olefin composition contains a significant amount of 1-butene and cis and trans-2-butene. Other minor components can include isobutene, butane, as well as $C_5$ and $C_6$ hydrocarbon.

The olefin product from the oxygenate conversion reaction, with or without prior separation of ethylene and propylene, then contacts another zeolite catalyst in a second stage. This catalyst in the second stage, according to one embodiment is a 10-ring zeolite, including but not limited to, ZSM-22, ZSM-23, ZSM-35, ZSM-42, or mixtures thereof. The catalyst in another embodiment is selected from the group comprising ZSM-22, ZSM-35 or mixtures thereof. In yet another embodiment, the catalyst is ZSM-35.

A two stage process can be designed so that the reaction takes place in a single reactor. For example, stacked catalyst beds, each bed containing a different zeolite catalyst can be used. Alternatively, a mixture of zeolite catalysts can be contained within a single fixed bed reactor or used concurrently in a fluidized-bed or a riser reactor.

In another embodiment, two or more reactors can be used in series. In this embodiment, an upstream or first stage reactor can contain a ZSM-5, and a downstream or second stage reactor can contain ZSM-22 or ZSM-35.

A multiple reactor design can provide additional operational controls for each of the respective stages of the invention. As a result, operational conditions for increasing the production of ethylene and propylene in each stage of the invention can be achieved. The catalyst used in each stage can also have different lifetimes and regeneration characteristics. As a result, operational parameters related to catalyst regeneration and/or catalyst lifetimes can be separately optimized for each stage in the multiple reactor design.

In one embodiment, a fixed-bed or fluidized bed reactor is used as a first stage reactor and the second stage reactor is a riser reactor. According to another embodiment, the riser reactor is positioned inside the first stage reactor to take advantage of the heat transfer requirements for each of the stages. Because the conversion of oxygenate to olefin is an exothermic process and the cracking of $C_4^+$ olefin to ethylene and propylene is an endothermic process, the heat generated in the first stage can be used to drive the second stage.

In the two stage process, the ethylene and propylene produced accounts for at least 60 percent by weight, and more preferably at least preferably at least 65 percent by weight, and more preferably at least 70 wt. % of the carbon in the oxygenate. Also, the amount of ethylene accounts for at least 25% by weight of the carbon in the oxygenate feed and more preferably at least 30% by weight of the carbon in the oxygenate feed. The amount of propylene in the two stage process accounts for at least 25 wt. % more preferably at least 30 wt. %, even more preferably 35 wt. %, and most preferably 40 wt. % of the carbon in the oxygenate feed.

The first stage of the process of the invention converts an oxygenate, preferably methanol and/or dimethyl ether, to a light olefin stream in which the ethylene, propylene, and butenes comprise over 40 wt. %, and typically over 60 wt. % of the olefin product produced in the oxygenate conversion process. Also, it is desirable for the ethylene and propylene to comprise more than 80 wt. %, preferably more than 95 wt. %, of the $C_2$ and $C_3$ components, respectively.

In one embodiment, the zeolite employed in the first stage of the process of the invention is ZSM-5 having a silica to alumina molar ratio of at least 250, as measured prior to any treatment of the zeolite to adjust its diffusivity. ZSM-5 and the preparation thereof is described in U.S. Pat. No. 3,702,886, the disclosure of which is incorporated herein by reference. The ZSM-5 catalyst will have a diffusivity of 0.1 sec$^{-1}$ to 20 sec$^{-1}$ and most typically of 0.2 sec$^{-1}$ to 5 sec$^{-1}$.

The pore structure of a ZSM-5 catalyst can be modified by steaming the zeolite molecular sieve as described in U.S. Pat. No. 6,048,816 to controllably reduce the micropore volume of the catalyst to not less than 50%, and preferably from 50% to 90%, of that of the unsteamed zeolite molecular sieve. The reduction in micropore volume is determined by measuring the n-hexane adsorption capacity of the molecular sieve, before and after steaming at 90° C. and 10 kPa (75 torr) n-hexane pressure. Steaming of the zeolite molecular sieve occurs at a temperature of at least 850° C., preferably from 950° C. to 1075° C., and most preferably from 1000° C. to 1050° C. for 10 minutes to 10 hours, preferably from 30 minutes to 5 hours.

According to one embodiment, the zeolite is modified with a phosphorous containing compound to control reduction in pore volume. Alternatively, the zeolite is steamed, and the phosphorous compound is added prior to or after steaming. The amount of phosphorous, as measured on an elemental basis, is from 0.05 wt. % to 20 wt. %, and preferably is from 1 wt. % to 10 wt. %, based on the weight of the zeolite molecular sieve. Preferably, the atomic ratio of phosphorus to framework aluminum (i.e. in the zeolite framework) is no greater than 4:1 and more preferably from 2:1 to 4:1.

Incorporation of a phosphorus modifier into the catalyst of the invention is accomplished, according to one embodiment, by contacting the zeolite molecular sieve either alone or the zeolite in combination with a binder with a solution of an appropriate phosphorus compound. The solid zeolite or zeolite catalyst is separated from the phosphorous solution, dried and calcined. In some cases, the added phosphorous is converted to its oxide form under such conditions. Contact with the phosphorus-containing compound is generally conducted at a temperature from 25° C. to 125° C. for a time from 15 minutes to 20 hours. The concentration of the phosphorus in the zeolite may be from 0.01 wt. % to 30 wt. %.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R3P=O$, $R_3P=S$, $RPO_2$, $RPS_2$, $RP(O)(OX)_2$, $RP(S)(SX)_2$, $R_2P(O)$ $OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)$ R, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite.

After contacting with the phosphorus-containing compound, the porous crystalline material, according to one embodiment, is dried and calcined to convert the phosphorus to an oxide form. Calcination is carried out in an inert atmosphere or in the presence of oxygen, for example, in air at a temperature from 150° C. to 750° C., preferably from 300° C. to 500° C., for at least 1 hour, preferably from 3 hours to 5 hours.

According to an embodiment, the zeolite molecular sieve, e.g., the ZSM-5, ZSM-22, ZSM-23, ZSM-35, and ZSM-42 is combined with a variety of binder materials. Such materials include materials such as clays, silica and/or metal oxides such as alumina. The latter is either naturally occurring or in the form of gelatinous precipitates or gels including mixtures of silica and metal oxides. Some binder materials also serve as diluents to control the rate of conversion from feed to products to minimize the capital costs of process units, such as heat exchangers, ordinarily used to control conversion rates and reaction zone temperatures. The presence of hot spots on the catalysts are also minimized. The binders, according to one embodiment, improve the crush strength of the catalyst under commercial operating conditions.

Naturally occurring clays, in some cases, are composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays are used in the raw state as originally mined or initially subjected to calcination, acid treatment or chemical modification.

In addition to the foregoing materials, the porous crystalline material are composited with a porous binders such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia according to one embodiment. Procedures for preparing silica-bound zeolites, such as ZSM-5, are described in U.S. Pat. Nos. 4,582,815; 5,053,374; and 5,182,242.

The relative proportions of zeolite molecular sieve and binder can vary widely, with the content of the zeolite ranging from about 2 to about 90% by weight, preferably about 10 wt. % to about 80 wt. % of the calcined catalyst. Preferably, the binder material is silica or a kaolin clay. The resulting catalyst may be formed using conventional processes, including spray-drying and extrusion, to form catalyst having a particle size of from about 20 microns to about 200 microns. The zeolite contained in the catalyst should have a crystal size less than about 10 microns, preferably less than about 5 microns, more preferably less than about 2 microns.

In one embodiment, the first stage occurs in a moving or fluid catalyst bed with continuous regeneration. The extent of coke loading is continuously controlled by varying the severity and/or the frequency of regeneration. The oxygenate conversion process is conducted at a temperature of at least 300° C., preferably from about 350° C. to about 600° C., more preferably from about 360° C. to about 480° C., and a pressure from about 15 psi (100 kPa) to about 1000 psi (7000 kPa). The oxygenate in the process is preferably methanol, dimethyl ether, or a mixture of methanol and dimethyl ether. The oxygenate or mixture of oxygenates can also be mixed with other feed components, such as hydrocarbons or inerts.

In this invention, a feed containing an oxygenate, and optionally a diluent or a hydrocarbon added separately or mixed with the oxygenate, is contacted with a catalyst molecular sieve in a reaction vessel or a reaction zone of an apparatus. The zone in which such contact takes place is herein termed the "reactor," which may be a part of a "reactor apparatus" or "reaction system." According to an embodiment, another part of the reaction system is a "regenerator," which comprises a volume wherein carbonaceous deposits (or coke) on the catalyst resulting from the olefin conversion reaction are removed by contacting the catalyst with regeneration medium.

One or more inert diluents may be present in the oxygenate feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially alkanes such as methane, ethane, and propane), essentially non-reactive alkylenes, essentially non-reactive aromatic compounds, and mixtures thereof. Preferred diluents are water and nitrogen. Water can be injected in either liquid or vapor form. For example, the process may be conducted in the presence of water such that the molar ratio water to methanol in the feed is from about 0.01:1 to about 10:1.

It is desirable in this invention that the oxygenate feed comprise at least about 50 wt. % oxygenate. Higher concentrations of oxygenates in the feed will be more efficient. Increasing concentrations to at least about 60, 70, 80, 90, 95 and 98 wt. % are increasingly effective.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, paraffins, alkylaromatics, aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of the olefin product.

In the process of this invention, coked catalyst can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. This type of regeneration process is typically utilized in a fixed bed or stacked catalyst bed reactor. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Any standard reactor system can be used, including fixed bed, fixed stacked bed, fluid bed or moving bed systems. Preferred reactors are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to about 1000 $hr^{-1}$, more preferably in the range of from about 20 $hr^{-1}$ to about 1000 $hr^{-1}$, and most preferably in the range of from about 20 $hr^{-1}$ to about 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The conversion of oxygenates to produce light olefins may be carried out in a variety of catalytic reactors. Reactor types include conventional reactors such as fixed-bed reactors, fluid bed reactors, and riser reactors. These and other types of conventional reactors are described in *Fluidization Engineering*, D. Kunii and O. Levenspiel, Robert E. Krieger Publishing Co. NY, 1977. Preferred reactors are riser reactors. Conventional riser reactor design is further described in "Riser Reactor," *Fluidization and Fluid-Particle Systems*, pages 48-59, F.A. Zenz and D. F. Othmer, Reinhold Publishing Corp., NY (1960), the description of which is incorporated herein by reference.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply gaseous $O_2$, preferably in the form of air. The $O_2$ or air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

The second stage of the process of the invention converts the $C_4^+$ olefin produced in the first stage oxygenate conversion to additional ethylene and propylene. The zeolite used in the second stage of the process is desirably ZSM-22 or ZSM-35. ZSM-22 and ZSM-35, and the preparation thereof, is described in U.S. Pat. No. 4,016,245, the disclosure of which is incorporated herein by reference.

The product stream from the first stage oxygenate conversion zone can be directed to the second stage cracking zone without prior separation of the produced ethylene and propylene because the ethylene and propylene are not likely to be significantly affected by contact with the ZSM-35 or ZSM-22 catalyst. However, it is desirable to separate a portion of the ethylene and propylene from the $C_4^+$ olefin in the first stage olefin product, because 30 to 60 percent by weight of the oxygenate conversion product can be ethylene and propylene. As a result, the feed volume processed in the second stage would be significantly reduced. This means that a more concentrated $C_4^+$ olefin composition can be more effectively converted to ethylene and propylene by contacting with a second zeolite.

It is desirable, therefore, that a butylene containing stream be separated and contacted with a second zeolite catalyst. It is desirable to separate out a butyelene stream containing at least about 20 wt. % butylene. Higher concentrations of butylenes will be more efficient. Increasing concentrations to at least about 40, 50, 60, 70, 80 and 90 wt. % are increasingly effective and desirable.

One particular embodiment of the invention is shown in FIG. 1. The reaction system can include a single reactor 10 with a stacked bed configuration. The oxygenate 12 will contact the first zeolite catalyst bed 14, preferably a ZSM-5 catalyst bed, whereby the methanol is converted to about 10 to 40% ethylene, 10 to 40% propylene, and 5 to 30% butenes, and 5 to 20% pentenes. Other higher olefin and paraffin products as well as some aromatics are also included in the conversion product, though in relatively smaller amounts.

The conversion product then contacts the second zeolite catalyst bed 16, preferably ZSM-22, or ZSM-35, more preferably ZSM-35, whereby a portion of the butenes and pentenes are converted to additional ethylene and propylene. Some aromatic product is also produced. A product stream 18 is then directed to one or more fractionators 20, 22 to separate into an ethylene stream 21, a propylene stream 23, and a $C_4^+$ stream 24. The $C_4^+$ stream 24 can contain mostly paraffins and aromatics, and can be used as a fuel source in the process. A portion of the stream 24 may also be recycled to the reactor 10 or the oxygenate feed 12.

In another embodiment, the first stage catalyst is mixed with the second stage catalyst in a single, fixed-bed, fluidized bed, or riser reactor. The proportion of the first stage catalyst to the second stage catalyst varies from 20 wt. % to 80 wt. % of the catalyst in the process with the second stage catalyst accounting for the difference.

Figure 2:
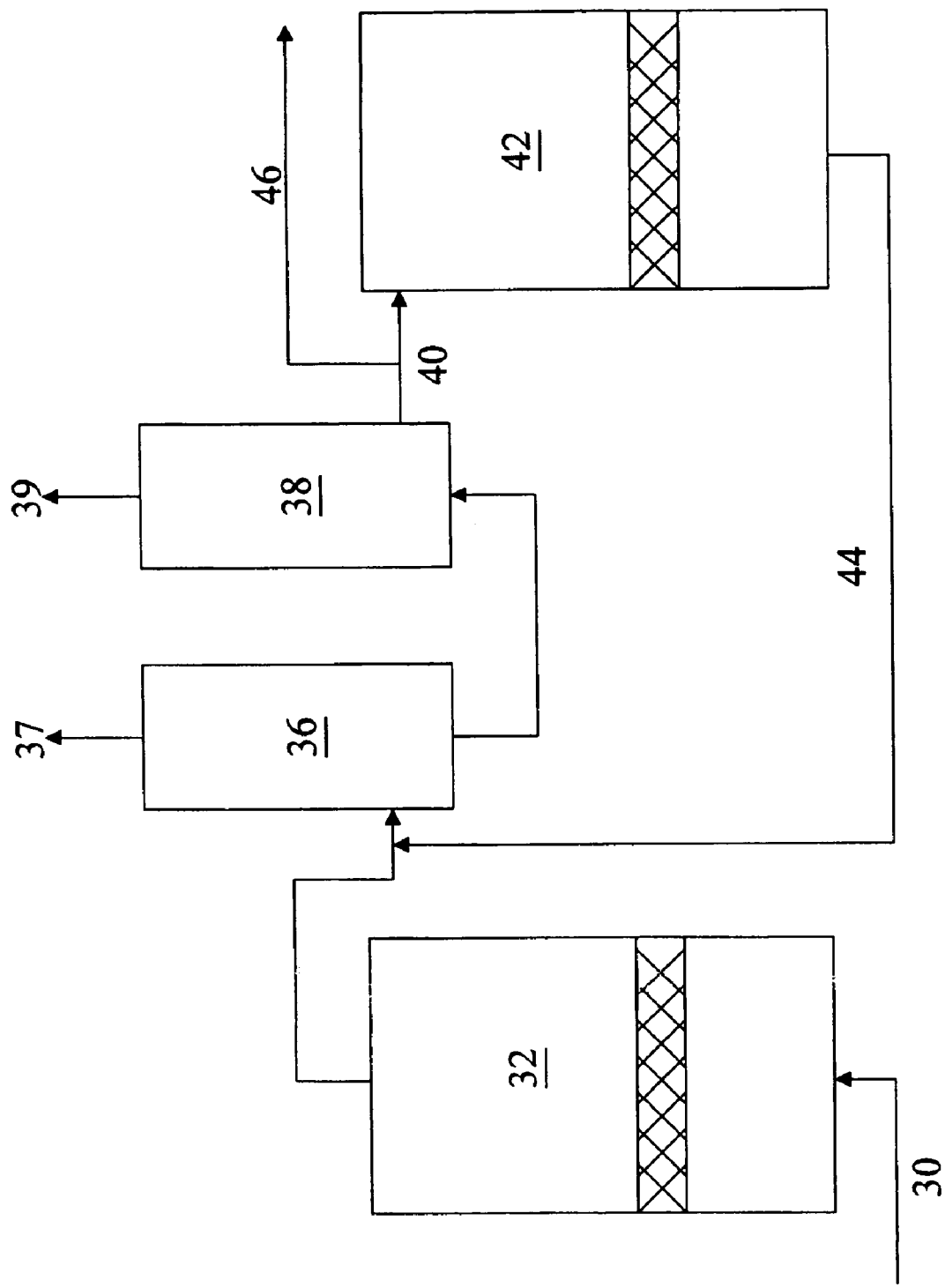
FIG. 2 is a schematic of a series of fixed-bed reactors where a portion of the desired ethylene and propylene is separated prior to contacting the second reactor.
Figure 3:
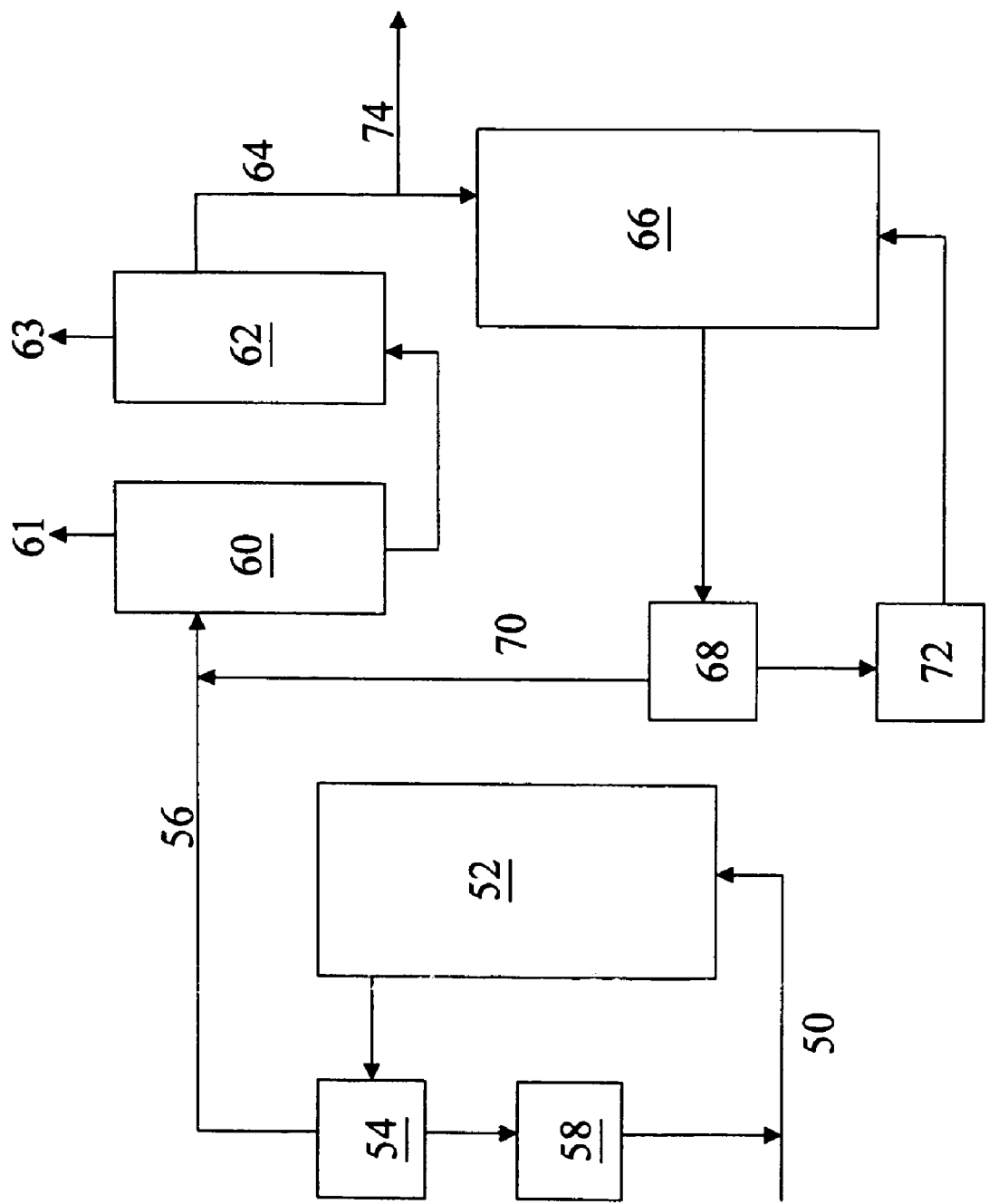
FIG. 3 is a schematic of a fluidized-bed reactor where a portion of the desired ethylene and propylene is separated prior to contacting the second fluidized-bed reactor.

Other embodiments of the invention include at least two reactors in series, as shown in FIGS. 2 and 3. The reactors can be of the fixed bed or fluidized-bed type, a riser reactor, or any combination thereof. In the case of either a fluidized-bed or riser reactor the reactor may also have a separate regeneration unit separate from the reactor itself or contained within the reactor.

As shown in FIG. 2, an oxygenate stream 30 is directed to a first stage fixed-bed reactor 32 containing a ZSM-5 catalyst. The resulting olefin product is sent via a line 34 to a series of fractionators 36, 38, where an ethylene stream 37 and a propylene stream 39 are removed. A $C_4^+$ olefin stream is also removed and sent via a line 40 to a second stage fixed-bed reactor 42 containing ZSM-22, or ZSM-35, preferably ZSM-35. The $C_4^+$ olefin is used as a feed to produce additional ethylene and propylene which is separated from the product stream 44. A portion of the separated hydrocarbon 40 feed is purged through a purge stream 46 to maintain an optimal level of inerts, paraffin and aromatics in the process. The purge stream 46 can be used as a fuel source for the process.

It is to be understood that a process of the invention includes fixed bed reactors in series such that the oxygenate conversion product from the first stage reactor is directed to the second stage reactor without separation of the desired ethylene and propylene. Instead, the primary ethylene and propylene separation takes place following the second stage reactor.

An alternative embodiment is shown in FIG. 3. In this embodiment, a methanol feed 50 is directed to a first stage fluidized bed reactor 52 containing a ZSM-5. The resulting oxygenate conversion product and portions of the catalyst are directed to a cyclone separator 54 where catalyst is separated from the oxygenate conversion product. The oxygenate conversion product is passed through a line 56, and the separated catalyst is directed to a regenerator 58. Regenerated catalyst is eventually fed back to the reactor 52.

The oxygenate conversion product is directed to a series of fractionators 60, 62, and ethylene and propylene are removed as an ethylene stream 61 and a propylene stream 63, respectively. $C_4^+$ olefin is removed through a line 64, and directed to a second stage fluidized bed reactor 66 containing ZSM-22, or ZSM-35, preferably ZSM-35. The $C_4^+0$ olefin is used as a feed to produce additional ethylene and propylene.

Hydrocarbon product and portions of the catalyst are directed to a cyclone separator 68 where the catalyst is separated from the hydrocarbon product. The hydrocarbon product is removed through a line 70, and the catalyst is directed to a regenerator 72. Regenerated catalyst is eventually fed back to the reactor 66. The hydrocarbon product is directed to the series of fractionators 60, 62. A portion of the $C_4^+$ olefin is purged from the process through a line 74 to maintain an optimal level of inerts, paraffin and aromatics in the process. The purge stream 74 can be used as a fuel source for the process.

If the first stage process is a highly exothermic process, and the second stage process is a highly endothermic process, then it would be desirable to have a first stage reactor and a second stage reactor that share their respective heat transfer functions. It would be particularly desirable to have first and second stage reactors thermally coupled. That is, it would be desirable to use heat produced by the first stage process to provide some or all of the heat requirements for the second stage process. The heat transfer between the first stage reactor and the second stage reactor can be carried out by conventional heat transfer equipment.

Figure 4:
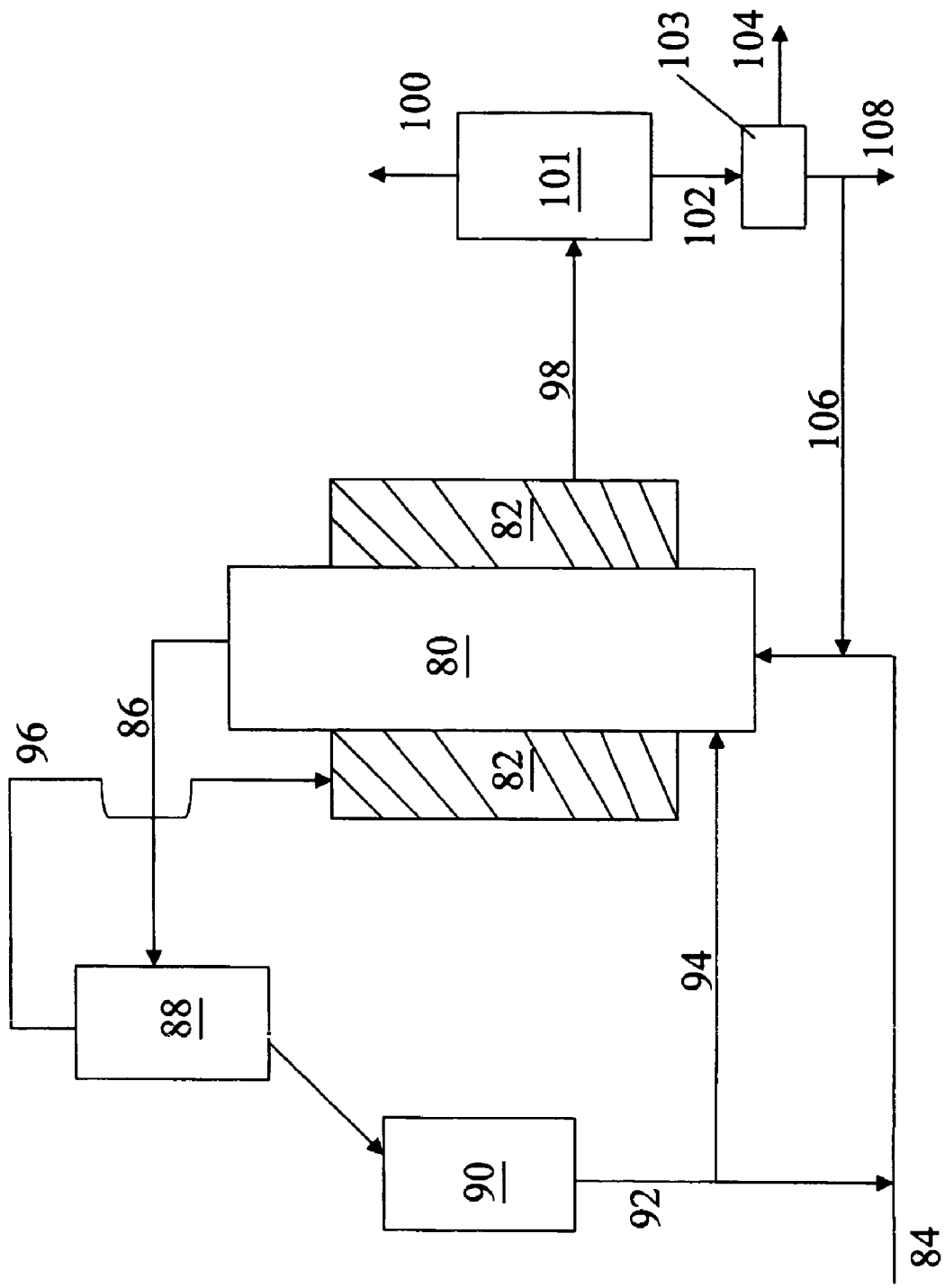
FIG. 4 is a schematic of a riser reactor that is in contact with the second stage reactor, and the olefin separation unit positioned after the second stage reactor.

Alternatively, as shown in FIG. 4, a first stage reactor 80 can be in contact with a second stage reactor 82. The first stage reactor 80 is preferably a riser reactor that is in contact with the second stage reactor 82, which can be a conventional fixed-bed or fluidized-bed reactor.

Oxygenate is directed through a line 84 to a first stage reactor 80. Product from the first stage is directed through a line 86 to a cyclone separator 88 where product is separated from the zeolite catalyst. Separated zeolite catalyst is directed to a regenerator 90 where coke is removed. Regenerated catalyst is returned to the first stage reactor 80 via a stream 94 and/or mixed with the oxygenate feed in line 84 before being directed back to the first stage reactor 80.

Product hydrocarbon removed by cyclone separator 88 is sent through a line 96 to the second stage reactor 82. Product from the second stage reactor 82 is sent through a line 98 to a separation unit 101. A $C_3^-$ fraction is separated and removed through a 100 and a $C_4^+$ fraction is removed through a line 102. The $C_4^+$ fraction is further separated in a separation unit 103 to remove aromatics, such as toluene and xylenes produced by the process. The aromatics are removed via a line 104. The remainder of the $C_4^+$ fraction is directed back to the first stage reactor 80 or mixed with the oxygenate feed 84 as shown by stream 106. A purge stream 108 is used to maintain an optimal level of inerts and light paraffin in the process.

Figure 5:
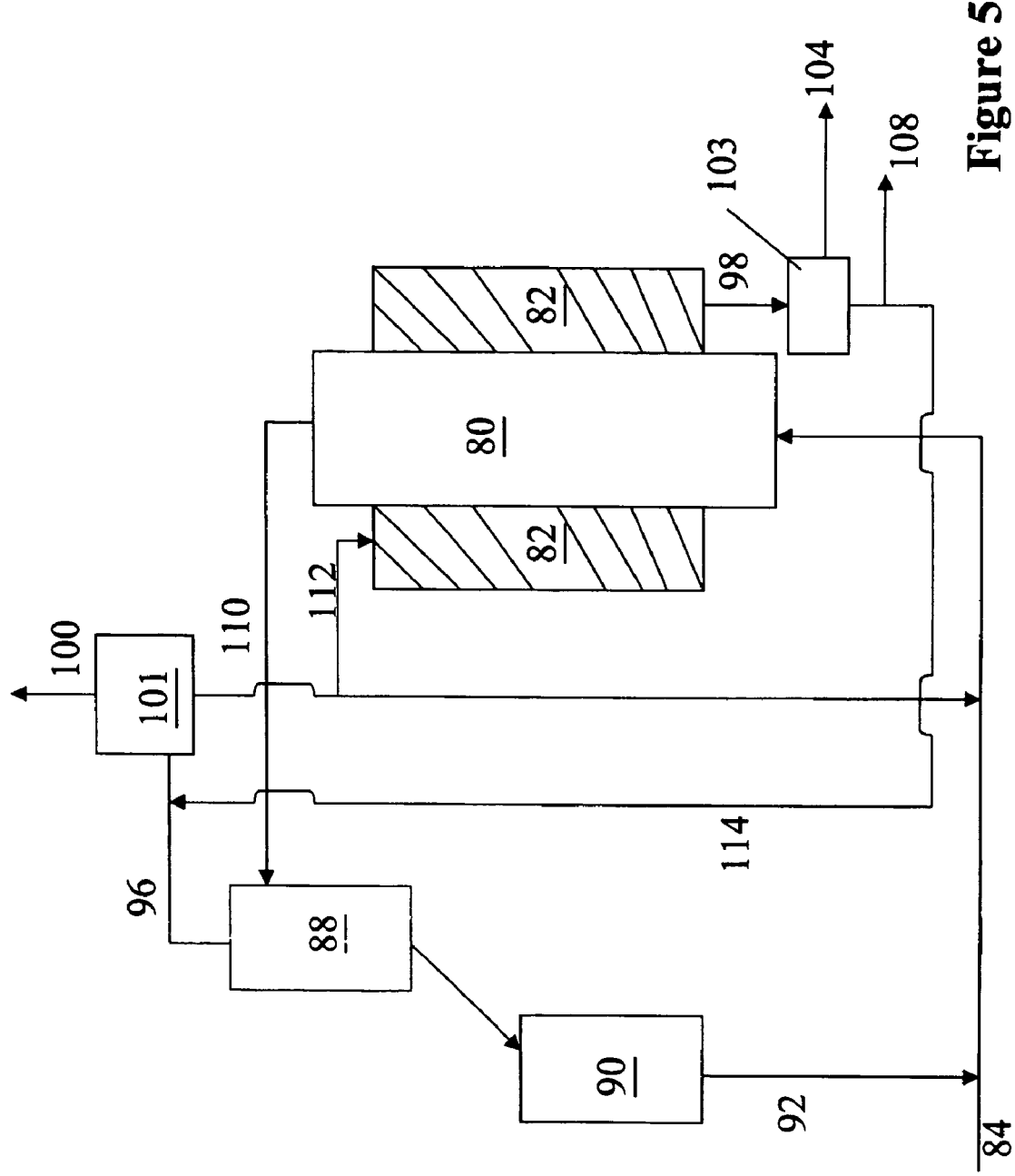
FIG. 5 is a schematic of a riser reactor that is in contact with the second stage reactor, and the olefin separation unit positioned before the second stage reactor.

FIG. 5 shows an embodiment in which a portion of the ethylene and propylene produced in a first stage reactor 80 can be separated from the total product hydrocarbon by a separator 101, and removed through a line 100. $C_4^+$ olefin which is also separated in separator 101 is removed through a line 110 and sent by a second line 112 to a second stage reactor 82. The separated $C_4^+$ olefin can contain up to 10 wt. %, preferably less than 5 wt. %, $C_2$ and $C_3$ hydrocarbon.

A portion of the $C_4^+$ olefin continues through line 110, combines with line 84, and is recycled back to the first stage reactor 80. Olefin product is removed from second stage reactor 82 and sent through line 98 to a separation unit 103, where the $C_4$ and higher hydrocarbons are removed through a line 104. The remainder of the product from the second stage reactor 82 is directed to the $C_3$ separation unit 101 via stream 114. $C_1$ to $C_3$ hydrocarbons are further separated to give the desired ethylene and propylene products. A purge stream 108 is used to maintain an optimal level of inerts and light paraffin in the process.

One skilled in the art will also appreciate that the ethylene and propylene produced by the invention can be polymerized to form polyolefins, particularly polyethylene and polypropylene respectively. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

In addition to polyolefins, numerous other olefin derivatives may be formed from the olefins recovered therefrom. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention is further described in the following examples, which represent various embodiments of the overall invention.

EXAMPLE 1

Separate feeds of butenes, pentenes and hexenes are contacted with ZSM-5, ZSM-35, and ZSM-22 at about 650° C. The product is recovered and analyzed for ethylene, propylene and aromatics content. The results are shown in Table 1.

TABLE 1

|  | ZSM-5 | | | ZSM-35 | | | ZSM-22 | | |
| --- | --- | --- | --- | --- | --- | --- | --- | --- | --- |
|  | C2= | C3= | Arom | C2= | C3= | Arom | C2= | C3= | Arom |
| butenes | 28 | 22 | 28 | 56 | 20 | 5 | 30 | 21 | 8 |
| pentenes | 32 | 23 | 29 | 29 | 24 | 19 | 33 | 35 | 13 |
| hexenes | 31 | 28 | 24 | 26 | 40 | 4 | 25 | 44 | 14 |

The results indicate that ZSM-35 has a very high selectivity to ethylene when butylene is used as the feed, and a high selectivity to ethylene and propylene compared to ZSM-5. ZSM-22 also has a high selectivity to ethylene and propylene compared to ZSM-5.

EXAMPLE 2

Methanol is contacted with P-ZSM-5 at about 560° C., and the product is collected. A portion of the product is analyzed. The results of the analysis are shown in Table 2. The data in second column of Table 2 is consist with data disclosed in Sun, et al *J. Catal.*, Vol. 143, pp. 32-44 (1993), and Ohlmann, et al, *Studies of Surface Science Catalysis*, Vol. 65, pp. 1-20 (1991).

A portion of the product collected following contact with the P-ZSM-5 is further contacted with ZSM-35, also at about 560° C. The product formed from contacting the ZSM-35 is collected and analyzed. The results are also shown in Table 2.

TABLE 2

| Product Formed | Yield of Product From Contact With P-ZSM-5 (wt. %) | Yield of Product From Contact With ZSM-35 (wt. %) |
| --- | --- | --- |
| CH4 | 1 | 2 |
| C2= | 10 | 32 |
| C3= | 40 | 44 |
| C4= | 27 | 5 |
| C5= | 10 | 3 |
| Aromatics | 8 | 11 |
| Other | 4 | 3 |
| C2= + C3= | 50 | 76 |

The data show a significant increase of C2= and C3=olefins in the contact with the ZSM-35 at the expense of the C4= and C5=olefins formed in the first contact with the P-ZSM-5.

Having now fully described this invention, it will be appreciated by those skilled in the art that the invention can be performed within a wide range of parameters within what is claimed, without departing from the spirit and scope of the invention.

What is claimed is:

1. A method of making light olefins, comprising:
contacting an oxygenate feed with a first zeolite catalyst comprising a ZSM-5 molecular sieve in a first bed or reactor to form a first product; and
contacting at least a portion of the first product with a second zeolite catalyst comprising a zeolite molecular sieve selected from the group consisting of ZSM-22, ZSM-23, ZSM-35, ZSM-48, and mixtures thereof in a second bed or reactor separate from the first bed or reactor to form a second product wherein, the first and second zeolite catalysts are in separate beds or reactors.

2. The method of claim 1, wherein the oxygenate feed contains at least 70 wt. % oxygenate.

3. The method of claim 2, wherein the oxygenate feed contains at least 80 wt. % oxygenate.

4. The method of claim 3, wherein the oxygenate feed contains at least 90 wt. % oxygenate.

5. The method of claim 1, wherein the ZSM-5 molecular sieve is selected from the group consisting of an unmodified ZSM-5, a phosphorous modified ZSM-5, a steam modified ZSM-5 having a micropore volume reduced to not less than 50% of that of the tmsteamed ZSM-5, and mixtures thereof.

6. The method of claim 1, wherein the second zeolite catalyst comprises a zeolite molecular sieve selected from the group consisting of ZSM-22, ZSM-35, and mixtures thereof.

7. The method of claim 1, wherein the oxygenate feed is contacted in a first bed containing the first catalyst and the first product is contacted in a second bed containing the second zeolite catalyst.

8. The method of claim 1, wherein the oxygenate comprises methanol and the second product comprises the light olefins.

* * * * *